United States Patent [19]

Bürstinghaus et al.

[11] Patent Number: 4,568,669
[45] Date of Patent: Feb. 4, 1986

[54] CYCLOPROPYL-METHYL-(THIO)-PHOSPHORIC ACID AMIDES AND THEIR USE FOR CONTROLLING PESTS

[75] Inventors: Rainer Bürstinghaus, Weinheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 537,047

[22] Filed: Sep. 29, 1983

[30] Foreign Application Priority Data

Oct. 1, 1982 [DE] Fed. Rep. of Germany ....... 3236431

[51] Int. Cl.⁴ .................. A01N 57/32; C07F 9/24
[52] U.S. Cl. ................... 514/112; 260/940; 260/954; 260/958; 260/949; 514/128; 514/131; 514/137
[58] Field of Search .............. 260/958, 940, 949, 954; 514/112, 128, 131, 137

[56] References Cited

U.S. PATENT DOCUMENTS 4,296,108 10/1981 Burstinghaus et al. ............ 424/210

*Primary Examiner*—Anton H. Sutto
*Attorney, Agent, or Firm*—Keil & Weinkauf

[57] ABSTRACT

Cyclopropyl-methyl-(thio)-phosphoric acid amides of the formula

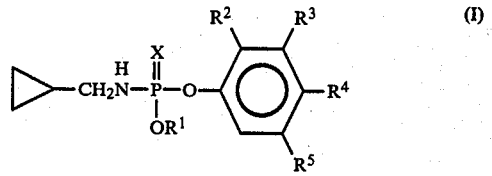

where $R^1$, $R^2$, $R^3$, $R^4$, $R^5$ and X have the meanings given in the claims and description, a process for their preparation and their use as pest control agents.

3 Claims, No Drawings

CYCLOPROPYL-METHYL-(THIO)-PHOSPHORIC ACID AMIDES AND THEIR USE FOR CONTROLLING PESTS

U.S. Pat. No. 4,296,108 and German Laid-Open Application DOS No. 2,934,229 disclose certain phosphoric acid amides substituted by cyclopropyl-methyl. They are suitable for controlling insects, arachnids and nematodes. However, their action is not always completely satisfactory, especially if a low concentration is applied.

We have found that cyclopropyl-methyl-(thio)-phosphoric acid amides of the formula I

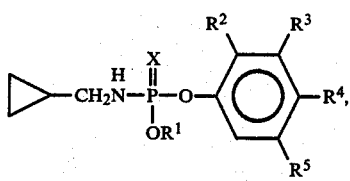

where $R^1$ is straight-chain or branched alkyl of not more than 4 carbon atoms, X is oxygen or sulfur and $R^2$, $R^3$, $R^4$ and $R^5$ can be identical or different and each is hydrogen, fluorine, chlorine, bromine, iodine, nitro, cyano, methyl, methylthio or trifluoromethyl, are superior to structurally similar active ingredients which are already known to have a good insecticidal, acaricidal and nematicidal action.

The cyclopropyl-methyl-(thio)-phosphoric acid amides of the formula I can be obtained by reacting a corresponding phenol (II) with a corresponding (thio)-phosphoric acid ester amide halide (III), hal(ogen) in formula III for economic reasons preferably being chlorine.

The reaction is advantageously carried out in a solvent or diluent, eg. an aliphatic or aromatic hydrocarbon, or chlorohydrocarbon, such as petroleum ether, benzene, toluene, xylene, gasoline, methylene chloride, chloroform, carbon tetrachloride, 1,2-dichloroethane or chlorobenzene, an ether, such as diethyl ether, di-n-butyl ether, methyl tert.-butyl ether, tetrahydrofuran or dioxane, a ketone, such as acetone, methyl ethyl ketone or methyl isopropyl ketone, a nitrile, such as acetonitrile or propionitrile, or a typical aprotic-dipolar substance, such as dimethylformamide or dimethylsulfoxide. Mixtures of these substances can also be used as the solvent or diluent.

The conventional bases for the phosphorylation of hydroxyl compounds are suitable acid acceptors, in particular alkali metal carbonates or alcoholates, such as sodium carbonate, methylate or ethylate and potassium carbonate, methylate or ethylate, and furthermore aliphatic, aromatic and heterocyclic amines, eg. triethylamine, dimethylamine, piperidine, dimethylaniline, dimethylbenzylamine and pyridine. In some cases, it is advantageous to use alkyl-lithium compounds, eg. n-butyl-lithium, or alkali metal hydrides, eg. sodium hydride.

Instead of adding an acid acceptor, it is also possible to prepare a salt of the phenol, for example an alkali metal, alkaline earth metal or ammonium salt, before the reaction and to use this.

The starting substances are usually employed in a stoichiometric ratio, but in individual cases an excess of one or other of the components may be definitely advantageous.

The reaction usually proceeds at a sufficient rate above room temperature. The temperature should generally not exceed 120° C. Since the reaction sometimes proceeds with the evolution of heat, it may be advantageous to provide a cooling possibility.

The reaction mixture is worked up in a conventional manner, for example by addition of water, separation of the phases, distillation, column chromatography and/or recrystallization.

The (thio)-phosphoric acid ester amide halides of the formula III are likewise novel. They can be obtained by reacting a (thio)-phosphoric acid O-alkyl ester dihalide with cyclopropylmethylamine, for example in accordance with the following equation:

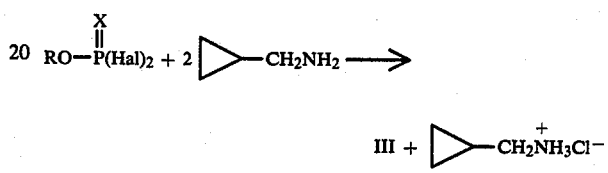

This reaction proceeds relatively vigorously; it takes place even at from −70° to +20° C., preferably from −30° to 0° C. One of the solvents or diluents mentioned is advantageously used.

The second molar equivalent of cyclopropylmethylamine can, in its function as acid acceptor, just as easily be replaced by a one-molar amount of a tertiary amine, eg. triethylamine, trimethylamine, N,N-dimethyl-N-ethylamine, pyridine or picoline.

Phenols of the formula II and their preparation are known (Houben-Weyl, Methoden der organischen Chemie, Edition, Volume VI/1c parts 1 and 2).

The cyclopropyl-methyl-(thio)-phosphoric acid amides (I) according to the invention are also obtained when a phosphoric acid phenyl ester halide IV

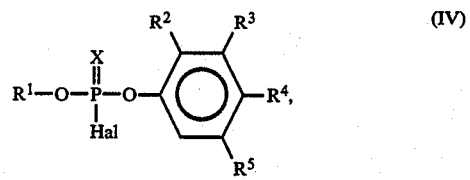

is first prepared (Houben-Weyl, Methoden der organischen Chemie, 4th Edition, Volume XII/2, pages 278, 279 and 612), and this is reacted with cyclopropylmethylamine (in not less than twice the molar amount). This reaction generally proceeds at below 120° C., preferably at from 20° to 60° C. The amine can be used in the pure form or as an aqueous solution; one of the above solvents or diluents may additionally be used. The substances according to the invention are usually obtained in the form of colorless or slightly brownish oils which can be freed from the last volatile constituents by prolonged heating to a moderately elevated temperature (incipient distillation) and can in this manner be purified. If crystalline compounds are obtained, these can generally be recrystallized.

The compounds I and III prepared as examples are characterized either by their melting point, their $^1H$—NMR spectrum or their IR spectrum, with typical absorption maxima from the so-called fingerprint range from 1,500 cm$^{-1}$ to 900 cm$^{-1}$.

Intermediates:

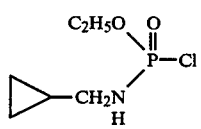

16.3 g of O-ethylphosphoric acid ester dichloride were dissolved in 80 ml of diethyl ether. A mixture of 7.1 g of cyclopropylmethylamine, 10.1 g of triethylamine and 45 ml of diethyl ether was run in at $-15°$ C. in the course of 60 minutes, while stirring vigorously. Stirring was continued at $-10°$ C. for 3 hours, the hydrochloride precipitated was filtered off and the filtrate was concentrated under reduced pressure from a water pump. The oil which remained was taken up in a 5/1 mixture of hexane and di-ethyl ether and the mixture was cooled to 0° C. and filtered again. After the last residues of solvent had been removed—finally at 30° C. under 0.01 mbar—16.0 g of O-ethyl-(N-cyclopropylmethyl)-phosphoric acid ester amide chloride were obtained as a colorless oil.

Yield: 81% of the calculated amount.

60 MHz-$^1$H-NMR spectrum in CDCl$_3$ ($\delta$ values in ppm): 0.3 (2H); 0.6 (2H), 1.1 (1H); 1.4 (3H); 2.75–3.2 (2H); 4.0–4.65 (2H); and 4.5–5.2 (1H).

The following phosphoric acid ester amide chlorides were prepared in comparable yield in a similar manner:

O-Methyl-(N-cyclopropylmethyl)-phosphoric acid ester amide chloride

60 MHz-$^1$H-NMR spectrum in CDCl$_3$ ($\delta$ values in ppm): 0.25 (2H); 0.6 (2H); 1.1 (1H); 2.7–3.2 (2H); 3.9 (3H); and 4.6–5.3 (1H).

O-Ethyl-(N-cyclopropylmethyl)-thiophosphoric acid ester amide chloride

60 MHz-$^1$H-NMR spectrum in CDCl$_3$ ($\delta$ values in ppm): 0.25 (2H); 0.6 (2H); 1.1 (1H); 1.45 (3H); 2.7–3.25 (2H); 3.5–4.5 (1H): and 3.95–4.5 (2H).

O-Methyl-(N-cyclopropylmethyl)-thiophosphoric acid ester amide chloride

80-MHz—H—NMR spectrum in CDCl$_3$ ($\delta$ values in ppm): 0.3 (2H); 0.6 (2H); 1.1 (1H); 2.75–3.15 (2H); 3.5–4.2 (1H); and 3.8 (3H).

EXAMPLE 1

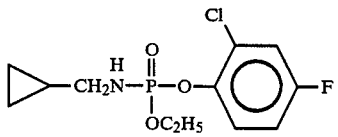

7.70 g of 2-chloro-4-fluorophenol and 9.87 g of O-ethyl-(N-cyclopropylmethyl)-phosphoric acid ester amide chloride were introduced into 50 ml of acetonitrile, and 6.90 g of finely powdered potassium carbonate were added in the course of 20 minutes, while stirring vigorously. Stirring was continued at 30° C. for 8 hours, the insoluble constituents were then filtered off with suction and the filtrate was concentrated under reduced pressure. The residue was taken up in ether, washed three times each with 5% strength sodium hydroxide solution and water, dried over sodium sulfate and freed from the solvent. After incipient distillation under 0.01 mbar at 50° C., 14.4 g of O-ethyl-O-(2-chloro-4-fluorophenyl)-(cyclopropylmethyl)-phosphoroamidate remained in the form of a clear, yellowish oil.

Yield: 94%.

$C_{12}H_{16}ClFNO_3P$ (307.5) calculated: C 46.8, H 5.2, N 4.6, found: C 46.7, H 5.4, N 4.7.

Infrared absorptions (cm$^{-1}$): 1,487, 1,188, 1,052, 1,039 and 890.

EXAMPLE 2

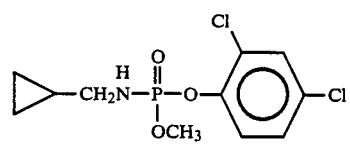

10.3 g of O-methyl-O-(2,4-dichlorophenyl)-(cyclopropylmethyl)-phosphoroamidate were obtained as a colorless oil in a yield of 72% in a manner similar to that in Example 1, by reacting 8.15 g of 2,4-dichlorophenol with 9.17 g of O-methyl-(N-cyclopropylmethyl)-phosphoric acid ester amide chloride and 6.9 g of potassium carbonate in 50 ml of acetone.

$C_{11}H_{14}Cl_2NO_3P$ (310), calculated: C 42.6, H 4.5, N 4.5, found: C 42.9, H 4.4, N 4.3.

Infrared absorptions (cm$^{-1}$): 1,475, 1,265–1,235, 110, 1,045 and 925.

EXAMPLE 3

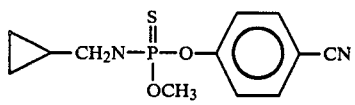

1.58 g of sodium hydride (as an 80% strength suspension in paraffin) were added to a solution of 5.95 g of 4-cyanophenol in 50 ml of tetrahydrofuran. The mixture was then stirred at room temperature for a further 3 hours and, when the evolution of hydrogen had ended, 9.98 g of O-methyl-(N-cyclopropylmethyl)-thiophosphoric acid ester amide chloride were added dropwise, during which the temperature rose to 32° C. After the mixture had been stirred at 65° C. for one day, the solvent was removed in a rotary evaporator, the residue was taken up in methyl tert.-butyl ether and the mixture was washed four times with 5% strength sodium hydroxide solution and three times with water. After drying over sodium sulfate, all the volatile constituents were stripped off at 45° C. under 0.02 mbar, 10.4 g of O-methyl-O-(4-cyanophenyl)-(cyclopropylmethyl)-phosphorothioamidate remaining as a yellowish oil.

Yield: 74%.

$C_{12}H_{15}N_2O_2PS$ (282), calculated: C 51.1, H 5.4, N 9.9, found: C 51.4, H 5.5, N 9.8.

Infrared absorptions (cm$^{-1}$): 1,499, 1,233, 1,081, 1,042 and 908.

EXAMPLE 4

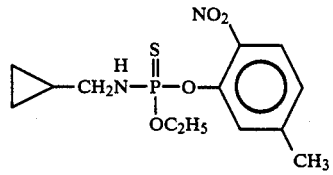

6.0 g of cyclopropylmethylamine were added dropwise to a solution of 11.9 g of O-ethyl-O-(2-nitro-5-methylphenyl)-thiophosphoric acid diester chloride in 60 ml of toluene, while cooling. The mixture was stirred at 20° C. for 12 hours and the hydrochloride precipitated was filtered off with suction and washed with water three times. After drying over sodium sulfate, the solvent was removed under reduced pressure and the residue was subjected to incipient distillation at 80° C. under 0.005 mbar. 11.3 g of O-ethyl-O-(2-nitro-5-methylphenyl)-(cyclopropylmethyl)-phosphoroamidate, which solidified to a yellowish solid, were obtained.

Melting point: 30.5°–31.5° C.

YIeld: 86%.

$C_{13}H_{19}N_2O_4PS$ (330) calculated: C 33.7, H 3.6, N 3.6, found: C 34.1, H 3.8, N 3.5.

Infrared absorptions ($cm^{-1}$): 1,357, 1,072, 1037 and 969.

The compounds listed below in Table I were each obtained by one of the routes described in Examples 1–4; other compounds corresponding to the formula (I) can be obtained in the same manner with appropriate alteration of the amounts given in the instructions and—in order to find the best reaction conditions—if necessary after a preliminary experiment.

| Ex. no. | $R^1$ | $R^2$ | $R^3$ | $R^4$ | $R^5$ | X | Infrared absorptions ($cm^{-1}$) |
|---|---|---|---|---|---|---|---|
| 5 | $C_2H_5$ | H | H | CN | H | O | 1497, 1240, 1040, 915 |
| 6 | $C_2H_5$ | H | H | $CF_3$ | H | O | 1323, 1238, 1123, 1102, 965, 942 |
| 7 | $C_2H_5$ | Cl | H | $CF_3$ | H | O | 1320, 1270, 1125, 1070, 1040 |
| 8 | $C_2H_5$ | $NO_2$ | H | H | $CH_3$ | O | 1453, 1375, 1248, 1044, 968 |
| 9 | $C_2H_5$ | H | $CH_3$ | $SCH_3$ | H | O | 1225, 1163, 1043, 1006, 961 |
| 10 | $C_2H_5$ | H | H | $SCH_3$ | H | O | 1486, 1220, 1041, 922 |
| 11 | $C_2H_5$ | H | H | $NO_2$ | H | O | 1516, 1345, 1240, 1040, 915 |
| 12 | $CH_3$ | Cl | H | Cl | Cl | O | 1465, 1350, 1250, 1225, 1115, 1083, 1050, 962 |
| 13 | $CH_3$ | H | H | CN | H | O | 1240, 1100, 1050, 920 |
| 14 | $CH_3$ | Cl | H | $CF_3$ | H | O | 1328, 1130, 1083, 1045 |
| 15 | $CH_3$ | H | H | $CF_3$ | H | O | 1330, 1240, 1122, 1105, 1070, 1050, 923 |
| 16 | $CH_3$ | Cl | H | F | H | O | 1489, 1246, 1190, 1042 |
| 17 | $CH_3$ | H | H | F | H | O | 1242, 1197, 1047, 920 |
| 18 | $CH_3$ | H | H | $SCH_3$ | H | O | 1486, 1219, 1170, 1100, 1048, 921 |
| 19 | $CH_3$ | H | H | $NO_2$ | H | O | 1346, 1240, 1110, 1048, 918 |
| 20 | $CH_3$ | H | $CH_3$ | $SCH_3$ | H | O | 1473, 1242, 1228, 1050, 962 |
| 21 | $CH_3$ | $NO_2$ | H | H | $CH_3$ | O | 1240, 1050, 1020, 970 |
| 22 | $C_2H_5$ | COO—i-$C_3H_7$ | H | H | H | S | 1295, 1257, 1080, 1035, 924 |
| 23 | $C_2H_5$ | H | H | $CF_3$ | H | S | 1320, 1165, 1123, 1065 |
| 24 | $C_2H_5$ | H | H | $NO_2$ | H | S | 1350, 1230, 1080, 1030, 900 |
| 25 | $C_2H_5$ | H | $CH_3$ | $NO_2$ | H | S | 1340, 1237, 1080, 1038, 1020, 965 |
| 26 | $C_2H_5$ | $NO_2$ | H | H | H | S | 1350, 1077, 1030, 1008 |
| 27 | $C_2H_5$ | Cl | H | Cl | H | S | 1472, 1060, 1034, 916 |
| 28 | $C_2H_5$ | H | H | $SCH_3$ | H | S | 1485, 1220, 1044, 922 |
| 29 | $C_2H_5$ | H | $CH_3$ | $SCH_3$ | H | S | 1241, 1227, 1045, 961 |
| 30 | $C_2H_5$ | Cl | H | Cl | Cl | O | 1462, 1348, 1249, 1083, 1045, 960 |
| 31 | $C_2H_5$ | Cl | H | Cl | H | O | 1474, 1060, 1040, 917 |
| 32 | $CH_3$ | H | H | $NO_2$ | H | S | 1491, 1346, 1234, 1081, 1042, 909 |
| 33 | $CH_3$ | H | H | F | H | S | 1195, 1083, 1044, 933, 913 |
| 34 | $CH_3$ | H | $CH_3$ | $NO_2$ | H | S | 1344, 1240, 1081, 1049, 1018, 969 |
| 35 | $CH_3$ | H | H | $SCH_3$ | H | S | 1459, 1213, 1081, 1044, 913 |
| 36 | $CH_3$ | H | $CH_3$ | $SCH_3$ | H | S | 1227, 1161, 1080, 1040, 1003, 958 |
| 37 | $CH_3$ | Cl | H | Cl | Cl | S | 1459, 1349, 1250, 1083, 1043, 957 |
| 38 | $CH_3$ | Cl | H | Cl | H | S | 1476, 1257, 1081, 1061, 1042, 917 |

The abovementioned active ingredients according to the invention, and others, are applied in the manner customary for phosphoric acid esters. Formulation details, information on applications, and data on suitable mixture components for achieving synergistic and other advantageous effects are given, for example, in U.S. Pat. Nos. 4,320,122 or 4,322,413, which are incorporated herein by reference.

As the examples which follow show, the cyclopropyl-methyl-(thio)-phosphoric acid amides according to the invention have an action on many species which is far better than, and an action on most species which is at least as good as, that of comparable prior art agents. The agents selected for comparison purposes were the commercial product Methamidophos

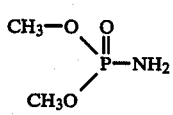

(I)

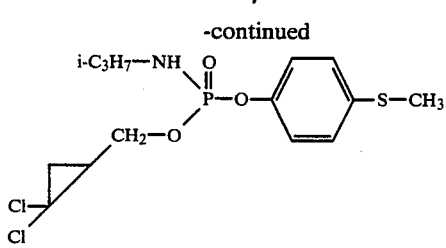
(II)

disclosed in German Laid-Open Application DE-OS No. 29 34 229.

USE EXAMPLE 1

Contact action on granary weevils (*Sitophilus granarius*)

Roughened glass plates measuring 8×8 cm were treated with acetonic solutions of the active ingredients.

After the solvent had evaporated, 100 granary weevils were placed on the plates, which were then covered with a watchglass (6 cm in diameter). After 4 hours the weevils were transferred to untreated vessels. The kill rate was determined after 24 hours by counting how many weevils were, after this period had elapsed, capable of leaving an untreated cardboard dish (40 mm in diameter, 10 mm high) within 60 minutes.

In this experiment, the compounds of Examples 2, 9, 10, 11, 18, 19, 20 and 24, at rates of from 0.01 to 0.05 mg, proved to be far more effective than comparative agents I and II, which had a comparable effect only at 0.1 mg.

USE EXAMPLE 2

Contact action on mosquito larvae (*Aedes aegypti*)

The active ingredient formulations were added to 200 ml of tapwater; 30 to 40 mosquito larvae in the 4th larval stage were then introduced.

The temperature was kept at 20° C. The action was determined after 24 hours.

In this experiment, the active ingredients of examples 9, 10, 11, 18, 19, 20 and 21 achieved, at a concentration of 0.01 ppm, 100% kill, whereas comparative agent I achieved less than 60% kill at a concentration of 1.0 ppm, and comparative agent II achieved 100% kill at a concentration of 0.025 ppm and less than 60% kill at a concentration of 0.01 ppm.

USE EXAMPLE 3

Contact action on houseflies (*Musca domestica*)

1 μl of acetonic solutions of the active ingredients was administered by means of a microsyringe to the ventral abdomen of 4-day old imagoes under slight $CO_2$ narcosis.

20 animals treated in the same way were then placed in a cellophane bag having a volume of approximately 500 ml.

After 4 hours, the animals in supine position were counted, and the $LD_{50}$ was worked out by means of a graph.

The active ingredients of Examples 5, 6, 13, 14 and 15 exhibited an $LD_{50}$ of 0.015 mg/fly, whereas comparative agent I had an $LD_{50}$ of 0.07 mg/fly.

USE EXAMPLE 4

Breeding experiment with houseflies (*Musca domestica*)

4.5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.

In this experiment, the active ingredients of Examples 2, 5, 6, 9, 10, 13, 14, 19 and 20 had a far better action than comparative agent I and an action which was at least 10 times better than that of comparative agent II.

USE EXAMPLE 5

Contact action on cotton stainers (*Dysdercus intermedius*)

Petri dishes 10 cm in diameter were lined with 1 ml of acetonic solutions of the active ingredients.

After the solvent had evaporated, 20 larvae in the penultimate stage were placed in each dish and the action was registered after 24 hours.

The active ingredients of Examples 9, 10, 11, 13, 14, 15, 18, 19, 20 and 24 had an action which was at least twice as good as that of comparative agents I and II.

USE EXAMPLE 6

Contact action and effect of ingested food on caterpillars of the diamondback moth (*Plutella maculipennis*)

Leaves of young cabbage plants were dipped for 3 seconds in aqueous emulsions of the active ingredients, and placed, after excess liquid had been briefly allowed to drip off, on a moist filter paper in a Petri dish. 10 caterpillars in the 4th stage were then placed on each leaf.

The action was assessed after 48 hours.

The active ingredients of Examples 6, 11, 19 and 22 were at least twice as effective as comparative agent I and at least 10 times more effective than comparative agent II.

USE EXAMPLE 7

Contact action on bean aphids (*Aphis fabae*), spray experiment

Potton bean plants (*Vicia faba*) with extensive bean aphid colonies were sprayed to runoff in a spray booth with aqueous formulations of the active ingredients.

The action was assessed after 48 hours.

In this test, the active ingredients of Examples 2, 6, 14, 15, 16, 18 20 and 30 had a better action than comparative agent I and an action which was from 20 to 100 times better than that of comparative agent II.

USE EXAMPLE 8

Action on spider mites (*Tetranychus telarius*)

Potted bush beans which had developed the first pair of true leaves and were under heavy attack from spider mites (*Tetranychus telarius*) of all stages were sprayed to runoff from all sides in a spray cabinet with aqueous formulations of the active ingredients. The plants were placed on a rotatable disc and were sprayed with 50 ml of spray liquor. Spraying lasted for about 22 seconds. The plants were investigated after 8 days for living spider mites.

In this test, the active ingredients of Examples 2, 5, 9, 10, 14, 16, 18, 21, 24 and 30 were at least twice as effective as comparative agent I.

USE EXAMPLE 9

Action on root-knot nematodes (*Meloidogyne incognita*) in tomatoes 30 ml of aqueous formulations of the active ingredients were intimately mixed with 300 g of mold heavily infested with *Meloidogyne incognita*. The mold was then filled into plastic pots and a tomato seedling planted therein. The pots were kept under greenhouse conditions at 22° to 24° C.

The roots were checked for root-knots after 6 to 8 weeks.

In this test, the active ingredients of Examples 5, 6, 9, 10, 11, 18 and 20 were fully effective at a concentration of less than 0.1, and some at less than 0.01%, whereas the comparative agents were ineffective at 0.1%.

We claim:

1. A cyclopropyl-methyl-(thio)-phosphoric acid amide of the formula

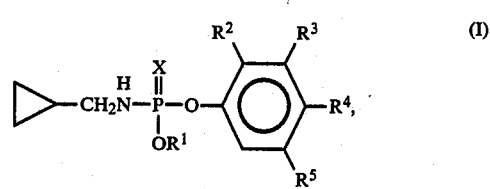

where $R^1$ is methyl or ethyl, X is oxygen or sulfur, $R^2$ is H, Cl, Br or $NO_2$; $R^3$ is H or $CH_3$; $R^4$ is H, CN, $CF_3$, $SCH_3$, $NO_2Cl$ or F and $R^5$ is H, $CH_3$ or Cl, with the proviso that at least one of $R^2$, $R^3$, $R^4$ or $R^5$ is not hydrogen.

2. A process for combating pests, wherein an effective amount of a cyclopropyl-methyl-(thio)-phosphoric acid amide of the formula I as set forth in claim 1 is allowed to act on the pests or their habitat.

3. A pesticide containing a solid or liquid carrier and at least one cyclopropyl-methyl-(thio)-phosphoric acid amide of the formula I as claimed in claim 1.

* * * * *